(12) United States Patent
Fujita et al.

(10) Patent No.: US 7,166,654 B2
(45) Date of Patent: Jan. 23, 2007

(54) ESTER COMPOUND, PLASTICIZER FOR BIODEGRADABLE ALIPHATIC POLYESTER RESIN, AND BIODEGRADABLE RESIN COMPOSITION

(75) Inventors: Yasunori Fujita, Kyoto (JP); Osamu Sawa, Suita (JP)

(73) Assignee: Daihachi Chemical Industry Co., Ltd., Osaka (JP)

( * ) Notice: Subject to any disclaimer, the term of this patent is extended or adjusted under 35 U.S.C. 154(b) by 0 days.

(21) Appl. No.: 10/509,793

(22) PCT Filed: Apr. 2, 2003

(86) PCT No.: PCT/JP03/04202

§ 371 (c)(1),
(2), (4) Date: Sep. 30, 2004

(87) PCT Pub. No.: WO03/087031

PCT Pub. Date: Oct. 23, 2003

(65) Prior Publication Data

US 2005/0228092 A1    Oct. 13, 2005

(30) Foreign Application Priority Data

Apr. 2, 2002   (JP) ............................. 2002-100337

(51) Int. Cl.
*C08K 5/11* (2006.01)
(52) U.S. Cl. ............... 523/124; 524/306; 524/308; 524/310; 524/311; 560/180; 560/190; 560/198; 560/199
(58) Field of Classification Search ............... 523/124; 524/306, 308, 310–311; 560/180, 190, 198–199
See application file for complete search history.

(56) References Cited

U.S. PATENT DOCUMENTS 2,325,983 A * 8/1943 Sarbach .................. 524/311
4,390,594 A   6/1983 Dages
4,459,311 A * 7/1984 DeTora et al. ............ 426/3
4,675,177 A * 6/1987 Geary ...................... 424/47
5,962,383 A * 10/1999 Doyel et al. .............. 510/164
6,415,614 B1 * 7/2002 Greenfield et al. ........ 62/112
6,515,054 B1 * 2/2003 Matsushita et al. ....... 524/167

FOREIGN PATENT DOCUMENTS

| EP | 1 153 602 A1 | 11/2001 |
|---|---|---|
| JP | 63-199794 | 8/1988 |
| JP | 04-335060 | 11/1992 |
| JP | 11-181262 | 7/1999 |
| JP | 2000-136300 | 5/2000 |
| JP | 2000-198908 | 7/2000 |
| JP | 2001-294736 | 10/2001 |
| JP | 2002-146170 | 5/2002 |
| WO | WO 94/06856 | 3/1994 |

OTHER PUBLICATIONS

Concise Statement of Relevancy of Cite Nos. 1–7 above.

* cited by examiner

*Primary Examiner*—Peter Szekely
(74) *Attorney, Agent, or Firm*—Knobbe Martens Olson & Bear LLP (57) ABSTRACT

An ester compound represented by formula (1)

$$R^1OOC-(CH_2)_m-COOR^2 \quad (1)$$

wherein $R^1$ and $R^2$ are different from each other and each represents a group of formula (2)

$$-(R^3O)_nR^4 \quad (2)$$

wherein $R^3$ is a $C_{1-6}$ alkylene group; $R^4$ is a $C_{1-10}$ straight- or branched-chain alkyl group, a $C_{6-12}$ aryl group, $C_{7-15}$ arylalkyl group or a $C_{7-15}$ alkylaryl group; m is an integer from 0 to 8, and n is an integer from 0 to 6.

This compound is suitable as a plasticizer for biodegradable aliphatic polyester resins.

17 Claims, 4 Drawing Sheets

ESTER COMPOUND, PLASTICIZER FOR BIODEGRADABLE ALIPHATIC POLYESTER RESIN, AND BIODEGRADABLE RESIN COMPOSITION

This application is the U.S. National Phase under 35 U.S.C. §371 of International Application PCT/JP03/04202, filed on Apr. 2, 2003, which claims priority of Japanese Patent Application No. 2002-100337, filed on Apr. 2, 2002. The International Application was published under PCT Article 21(2) in a language other than English.

TECHNICAL FIELD

The present invention relates to an ester compound for use as a plasticizer for biodegradable aliphatic polyester resins to be used in films, sheets and like molded articles that require flexibility, and a plasticizer for biodegradable aliphatic polyester resins that comprises the ester compound. The present invention also relates to a biodegradable resin composition comprising the plasticizer, and more specifically, a biodegradable resin composition that has excellent water resistance and that can be molded into an article from which the plasticizer is difficult to migrate (bleed out) to the surface.

BACKGROUND ART

Biodegradable and other naturally degradable polymers have been attracting attention from the viewpoint of environmental protection. Researchers are therefore conducting active research on poly(lactic acid)s, copolymers of lactic acid and other aliphatic hydroxycarboxylic acids, polyesters of aliphatic polyhydric alcohols with aliphatic polycarboxylic acids, and the like.

In particular, poly(lactic acid)s are preferable materials since they are produced from agricultural products and thus free from the problem of resource depletion. In recent years, L-lactic acid used as the raw material can be produced by fermentation in large quantities and at low cost. However, poly(lactic acid)s have the drawback of being rigid, brittle and inflexible because of their high crystallinity and rigid molecular structure. Therefore, poly(lactic acid)s per se are not suitable for applications that require flexibility, such as films and packaging.

Poly(lactic acid)s can be softened, for example, by adding plasticizers, blending soft polymers, or carrying out copolymerization. However, when blending soft polymers, usable soft polymers are limited to biodegradable resins such as polybutylene succinate from the viewpoint of biodegradability. Such biodegradable resins have to be added in large quantities to impart sufficient flexibility, and the addition in large quantities may impair this characteristic of poly(lactic acid)s. Copolymerization changes the physical properties such as melting point and heat resistance, owing to the decrease in crystallinity and glass transition temperature.

Further, when plasticizers are added, they are likely to migrate (bleed) to the surface, thereby staining the surface or impairing the transparency of the molded article. To solve this problem, various plasticizers as mentioned below have been proposed.

For example, Japanese Unexamined Patent Publication No. 1992-335060 discloses a composition comprising a poly(lactic acid) and a plasticizer, and shows diisopropyl adipate and dioctyl sebacate as effective plasticizers. However, their plasticizing effects are small and the composition is too inflexible to be used for general-purpose films. This publication also discloses diethyl phthalate as a phthalic acid plasticizer. However, diethyl phthalate has a low plasticizing effect and is likely to bleed out and volatilize.

Japanese Unexamined Patent Publication Nos. 1999-35808 and 1999-181262 disclose use of an ether ester plasticizer in a lactic acid polymer comprising a poly(lactic acid) as the main component. However, the ether ester plasticizer itself has insufficient water resistance, and when it is used in films or like molded articles, the molded articles have drawbacks such as low tensile strength.

Japanese Unexamined Patent Publication No. 2000-136300 discloses a lactic acid polymer comprising polypropylene glycol dibenzoate as a plasticizer. However, because of its poor compatibility with resins, this plasticizer has a low plasticizing effect and is difficult to use in general-purpose films.

Japanese Unexamined Patent Publication No. 2000-198908 discloses use of acetyl tributyl citrate, dioctyl phthalate or diisodecyl adipate singly as a plasticizer in a poly(lactic acid). However, these plasticizers easily bleed out and have a poor plasticizing effect.

Japanese Unexamined Patent Publication No. 2001-294736 discloses use of bis(butyldiglycol) adipate or the like singly as a plasticizer in a poly(lactic acid) as an aliphatic polyester resin. However, these plasticizers easily bleed out and have poor water resistance and low plasticizing effect.

Thus, no satisfactory plasticizers for biodegradable resins have been developed yet. One idea may be to use two or more plasticizers to compensate for each other's shortcomings. However, such use makes the production process complicated, and some plasticizers are difficult to mix uniformly because of their differences in compatibility with the base resin.

DISCLOSURE OF THE INVENTION

A first object of the present invention is to provide an ester compound that can be freely designed to have characteristics desired for plasticizers for biodegradable aliphatic polyester resins, a plasticizer for biodegradable aliphatic polyester resins that comprises such an ester compound, and a biodegradable resin composition comprising such an ester compound as a plasticizer.

A second object of the present invention is to provide an ester compound that, when used as a plasticizer for a biodegradable aliphatic polyester resin, makes a biodegradable resin composition that has high water resistance and from which the plasticizer is difficult to bleed out; a plasticizer for biodegradable resins that comprises such an ester compound; and a biodegradable resin composition that has high water resistance and from which the plasticizer is difficult to bleed out.

The present inventors conducted extensive research to achieve the above objects, and found that, when using an ester of an aliphatic polybasic acid with at least two members selected from the group consisting of alcohols and ether alcohols (hereinafter referred to as "mixed alcohol ester") as a plasticizer in aliphatic polyester resins, characteristics that cannot be obtained by single or combined use of esters of an aliphatic polybasic acid with one type of alcohol or ether alcohol (hereinafter referred to as "single alcohol ester") are achieved, in particular water resistance and non-bleeding properties. The present invention was thus accomplished.

The present invention has been achieved based on the above findings and provides the ester compounds and other items described below.

1. An ester compound represented by formula (1)

wherein $R^3$ and $R^2$ are different from each other and each represents a group of formula (2)

wherein $R^3$ is a $C_{1-6}$ alkylene group; $R^4$ is a $C_{1-10}$ straight- or branched-chain alkyl group, a $C_{6-12}$ aryl group, a $C_{7-15}$ arylalkyl group or a $C_{7-15}$ alkylaryl group; m is an integer from 0 to 8, and n is an integer from 0 to 6.

2. An ester compound represented by formula (3)

wherein $R^5$ is H, a $C_{1-5}$ aliphatic acyl group or a $C_{6-12}$ aromatic acyl group; and $R^6$, $R^7$ and $R^8$ each represent a group of formula (4) or (5)

wherein $R^9$ is a $C_{1-6}$ alkylene group; $R^{10}$ is a $C_{1-10}$ straight- or branched-chain alkyl group, a $C_{6-12}$ aryl group, a $C_{7-15}$ arylalkyl group or a $C_{7-15}$ alkylaryl group; and p is an integer from 0 to 6; and wherein $R^{11}$ is a $C_{1-6}$ alkylene group; $R^{12}$ is a $C_{1-10}$ straight- or branched-chain alkyl group, a $C_{6-12}$ aryl group, a $C_{7-15}$ arylalkyl group or a $C_{7-15}$ alkylaryl group; and q is an integer from 0–6;

with the proviso that the compound wherein $R^6 R^7$ and $R^8$ are the same is excluded.

3. A plasticizer for biodegradable aliphatic polyester resins, the plasticizer comprising an ester of an aliphatic polybasic acid with at least two members selected from the group consisting of alcohols and ether alcohols.

4. A plasticizer for biodegradable aliphatic polyester resins according to item 3, wherein the ester is a compound represented by formula (1)

wherein $R^1$ and $R^2$ are different from each other and each represents a group of formula (2)

wherein $R^3$ is a $C_{1-6}$ alkylene group, $R^4$ is a $C_{1-10}$ straight- or branched-chain alkyl group, a $C_{6-12}$ aryl group, a $C_{7-15}$ arylalkyl group or a $C_{7-15}$ alkylaryl group, m is an integer from 0 to 8, and n is an integer from 0 to 6.

5. A plasticizer for biodegradable aliphatic polyester resins according to item 3, wherein the ester is a compound represented by formula (3)

wherein $R^5$ is H, a $C_{1-5}$ aliphatic acyl group or a $C_{6-12}$ aromatic acyl group; and $R^6$, $R^7$ and $R^8$ each represent a group of formula (4) or (5)

wherein $R^9$ is a $C_{1-6}$ alkylene group; $R^{10}$ is a $C_{1-10}$ straight- or branched-chain alkyl group, a $C_{6-12}$ aryl group, a $C_{7-15}$ arylalkyl group or a $C_{7-15}$ alkylaryl group; and p is an integer from 0 to 6; and wherein $R^{11}$ is a $C_{1-6}$ alkylene group; $R^{12}$ is a $C_{1-10}$ straight- or branched-chain alkyl group, a $C_{6-12}$ aryl group, a $C_{7-15}$ arylalkyl group or a $C_{7-15}$ alkylaryl group; and q is an integer from 0 to 6;

with the proviso that the compound wherein $R^6$, $R^7$ and $R^8$ are the same is excluded.

6. Use of a compound according to item 1 as a plasticizer for biodegradable aliphatic polyester resins.

7. Use of a compound according to item 2 as a plasticizer for biodegradable aliphatic polyester resins.

8. A biodegradable resin composition comprising (i) a biodegradable aliphatic polyester resin and (ii) a plasticizer comprising an ester of an aliphatic polybasic acid with at least two members selected from the group consisting of alcohols and ether alcohols.

9. A biodegradable resin composition according to item 8, wherein the plasticizer is a compound represented by formula (1)

wherein $R^1$ and $R^2$ are different from each other and represents a group of formula (2)

wherein $R^3$ is a $C_{1-6}$ alkylene group; $R^4$ is a $C_{1-10}$ straight- or branched-chain alkyl group, a $C_{6-12}$ aryl group, a $C_{7-15}$ arylalkyl group or a $C_{7-15}$ alkylaryl group; m is an integer from 0 to 8, and n is an integer from 0 to 6.

10. A biodegradable resin composition according to item 8, wherein the plasticizer is a compound represented by formula (3)

wherein $R^5$ is H, a $C_{15}$ aliphatic acyl group or a $C_{6-12}$ aromatic acyl group; and $R^6$, $R^7$ and $R^8$ each represent a group of formula (4) or (5)

wherein $R^9$ is a $C_{1-6}$ alkylene group; $R^{10}$ is a $C_{1-10}$ straight- or branched-chain alkyl group, a $C_{6-12}$ aryl group, a $C_{7-15}$ arylalkyl group or a $C_{7-15}$ alkylaryl group; and p is an integer from 0 to 6; and $$—CH_2COO(R^{11}O)_qR^{12} \qquad (5)$$

wherein $R^9$ is a $C_{1-6}$ alkylene group; $R^{12}$ is a $C_{1-10}$ straight- or branched-chain alkyl group, a $C_{6-12}$ aryl group, a $C_{7-15}$ arylalkyl group or a $C_{7-15}$ alkylaryl group; and q is an integer from 0 to 6;

with the proviso that the compound wherein $R^6$, $R^7$ and $R^8$ are the same is excluded.

11. A biodegradable resin composition according to any one of items 8, 9 and 10, wherein the biodegradable aliphatic polyester resin is at least one member selected from the group consisting of resins obtainable by condensation of hydroxycarboxylic acid(s) and resins obtainable by condensation of aliphatic dicarboxylic acid(s) with aliphatic diol(s).

12. A resin composition according to item 11, wherein the biodegradable aliphatic polyester resin is a poly(lactic acid).

13. A resin composition according to item 11, wherein the biodegradable aliphatic polyester resin is polybutylene succinate, polybutylene succinate adipate or a mixture thereof.

14. A method for plasticizing a biodegradable aliphatic polyester resin, the method comprising adding to a biodegradable aliphatic polyester resin an ester compound represented by formula (1)

$$R^1OOC—(CH_2)_m—COOR^2 \qquad (1)$$

wherein $R^1$ and $R^2$ are different from each other and each represents a group of formula (2)

$$—(R^3O)_nR^4 \qquad (2)$$

wherein $R^3$ is a $C_{1-6}$ alkylene group; $R^4$ is a $C_{1-10}$ straight- or branched-chain alkyl group, a $C_{6-12}$ aryl group, a $C_{7-15}$ arylalkyl group or a $C_{7-15}$ alkylaryl group; m is an integer from 0 to 8, and n is an integer from 0 to 6.

15. A method according to item 14, wherein the biodegradable aliphatic polyester resin is a poly(lactic acid).

16. A method according to item 14, wherein the biodegradable aliphatic polyester resin is polybutylene succinate, polybutylene succinate adipate or a mixture thereof.

17. A method for plasticizing a biodegradable aliphatic polyester resin, the method comprising adding to a biodegradable aliphatic polyester resin an ester compound represented by formula (3)

(3)

wherein $R^5$ is H, a $C_{1-5}$ aliphatic acyl group or a $C_{6-12}$ aromatic acyl group; and $R^6$, $R^7$ and $R^8$ each represent a group of formula (4) or (5)

$$—(R^9O)_pR^{10} \qquad (4)$$

wherein $R^9$ is a $C_{1-6}$ alkylene group; $R^{10}$ is a $C_{1-10}$ straight- or branched-chain alkyl group, a $C_{6-12}$ aryl group, a $C_{7-15}$ arylalkyl group or a $C_{7-15}$ alkylaryl group; and p is an integer from 0 to 6; and $$—CH_2COO(R^{11}O)_qR^{12} \qquad (5)$$

wherein $R^{11}$ is a $C_{1-6}$ alkylene group; $R^{12}$ is a $C_{1-10}$ straight- or branched-chain alkyl group, a $C_{6-12}$ aryl group, a $C_{7-15}$ arylalkyl group or a $C_{7-15}$ alkylaryl group; and q is an integer from 0 to 6;

with the proviso that the compound wherein $R^6$, $R^7$ and $R^8$ are the same is excluded.

18. A method according to item 17, wherein the biodegradable aliphatic polyester resin is a poly(lactic acid).

19. A method according to item 17, wherein the biodegradable aliphatic polyester resin is polybutylene succinate, polybutylene succinate adipate or a mixture thereof.

The present invention provides an ester compound that can be freely designed to have characteristics desired in plasticizers for biodegradable aliphatic polyester resins, a plasticizer for biodegradable aliphatic polyester resins that comprises the ester compound, and a biodegradable resin composition comprising the ester compound as a plasticizer.

Specifically, the present invention provides an ester compound that, when used as a plasticizer for a biodegradable aliphatic polyester resin, makes a biodegradable resin composition that has high water resistance and from which the plasticizer is difficult to bleed out; a plasticizer for biodegradable aliphatic polyester resins that comprises the ester; and a biodegradable resin composition that has excellent water resistance and from which the plasticizer is difficult to bleed out.

More specifically, the ester compound of the present invention is an ester of an aliphatic polybasic acid with at least two members selected from the group consisting of alcohols and ether alcohols, and therefore it can be freely designed to have characteristics desired in plasticizers by selecting and combining alcohols and/or ether alcohols to be used.

Thus, the ester compound of the present invention is more advantageous than combinations of single alcohol ester compounds obtained by using a single type of alcohol or ether alcohol, since the ester compound of the present invention has the characteristics of individual single alcohol ester compounds, and further has effects that cannot be achieved by combined use of single alcohol ester compounds. Namely, the ester compound of the present invention has effects equal to or greater than those of combinations of single alcohol ester compounds.

Specifically, the ester compound of the present invention serves as a plasticizer having both non-bleeding properties and water resistance that cannot be realized by conventional single alcohol ester compounds. Further, the ester compound of the present invention remarkably improves the tensile modulus and elongation of resin molded articles that contain the ester compound, i.e., has an outstanding plasticizing effect. Accordingly, even a small amount of the ester compound, when added, imparts flexibility to relatively rigid biodegradable aliphatic polyester resins such as poly(lactic acid)s.

Furthermore, an aromatic ester group may be introduced into a dibasic acid ester (B1) or citric acid ester (B2) in order to improve the water resistance. For example, benzyl alcohol and diethylene glycol monomethyl ether are reacted with adipic acid to obtain benzyl methyldiglycol adipate. Use of the benzyl methyl diglycol adipate remarkably improves the tensile modulus, elongation and water resistance of resin molded articles that contain it, as compared with use of dibenzyl adipate or bis(methyl diglycol) adipate alone.

Combined use of two or more plasticizers requires troublesome procedures. Further, when two or more plasticizers are blended with a biodegradable aliphatic polyester resin, it is possible that the plasticizers do not uniformly mix with the resin owing to differences in their compatibility with the resin, thereby adversely influencing the properties of the resulting resin composition. In contrast, the ester compound of the present invention, even when used singly, exhibits remarkable effects, making the procedure simple and enabling uniform blending with biodegradable aliphatic polyester resins. The obtained resin composition is advantageous in that it is isotropic.

Furthermore, when the ester compound of the present invention is added to a transparent base resin such as a poly(lactic acid), the base resin retains its transparency.

Thus, when adding the ester compound of the present invention as a plasticizer to a biodegradable aliphatic polyester resin, a biodegradable resin composition is obtained which is excellent in flexibility and water resistance and which is free from plasticizer bleed-out. Further, when the ester compound of the present invention is mixed with a transparent base resin, a transparent biodegradable resin composition can be obtained. Accordingly, the biodegradable resin composition comprising the ester compound of the present invention as a plasticizer can be suitably used as materials for films, sheets, packaging and molded articles.

DETAILED DESCRIPTION OF THE INVENTION

The present invention will be described below in detail.

(I) Ester Compound

Basic Structure

The ester compound of the present invention is an ester of an aliphatic polybasic acid with two or more members selected from the group consisting of alcohols and ether alcohols.

First, explanations of single alcohol esters will be given. Polybasic acid esters with a single type of ester group are obtained by reacting a polybasic acid with a single type of alcohol or ether alcohol. For example, dimethyl adipate is obtained by reacting 1 mole of adipic acid with 2 moles of methanol. In contrast, when at least one additional alcohol or ether alcohol is used in the reaction of a polybasic acid with an alcohol or ether alcohol, a polybasic acid ester having different types of ester groups is obtained. According to the present invention, such an ester compound is referred to as "mixed alcohol ester". For example, methyl butyl adipate, a mixed alcohol ester, is obtained from 1 mole of adipic acid, 1 mole of methanol and 1 mole of butanol.

In the ester compound of the present invention, the aliphatic polybasic acid may be, but is not to limited to, a divalent or trivalent straight- or branched-chain saturated aliphatic polybasic acid. The aliphatic polybasic acid has about 2 to about 20, preferably about 4 to about 10, and more preferably about 4 to about 6, carbon atoms.

Alcohols usable in the invention include, but are not limited to, straight- or branched-chain saturated aliphatic alcohols or aromatic alcohols having usually about 1 to about 20, preferably about 4 to about 10, and more preferably about 4 to about 8, carbon atoms.

Usable ether alcohols include, but are not limited to, ethylene oxide adducts, propylene adducts, butylene adducts and the like of the above-mentioned alcohols. The preferable number of carbon atoms of such ether alcohols is usually about 3 to about 20, particularly about 3 to about 10, and more particularly about 5 to about 8.

Typical examples of ester compounds according to the present invention include a dibasic acid ester compound (B1) represented by formula (1) and a citric acid ester compound (B2) represented by formula (3).

Dibasic Acid Ester Compound (B1)

Of the mixed alcohol esters, the dibasic acid ester (B1) is a compound represented by formula (1)

$$R^1OOC-(CH_2)_m-COOR^2 \quad (1)$$

wherein $R^1$ and $R^2$ are different from each other and each represents a group of formula (2)

$$-(R^3O)_nR^4 \quad (2)$$

wherein $R^3$ is a $C_{1-6}$ alkylene group; $R^4$ is a $C_{1-10}$ straight- or branched-chain alkyl group, a $C_{6-12}$ aryl group, a $C_{7-15}$ arylalkyl group or a $C_{7-15}$ alkylaryl group; m is an integer from 0 to 8; and n is an integer from 0 to 6.

Examples of dibasic acids usable as starting materials for the dibasic acid ester (B1) include oxalic acid, malonic acid, succinic acid, glutaric acid, adipic acid, pimelic acid, suberic acid, azelaic acid, sebacic acid and the like. Among them, succinic acid and adipic acid are preferable.

Examples of alcohols usable as starting materials for the dibasic acid ester (B1) include methanol, ethanol, 1-propanol, 2-propanol, 1-butanol, 2-buthanol, 2-methyl-1-propanol, 1,1-dimethyl-1-ethanol, pentanol, hexanol, heptanol, octanol, phenol, benzyl alcohol, phenethyl alcohol and the like. Among them, methanol, ethanol, 1-propanol, 1-butanol, pentanol, hexanol, heptanol, octanol, benzyl alcohol, phenethyl alcohol and the like are preferable, and 1-butanol, octanol, benzyl alcohol and phenethyl alcohol are especially preferable.

Examples of ether alcohols usable as starting materials for the dibasic acid ester (B1) include ethylene oxide adducts and propylene oxide adducts and the like of the above-mentioned alcohols. Specific examples include ethylene glycol monomethyl ether, ethylene glycol monoethyl ether, ethylene glycol monobutyl ether, ethylene glycol monophenyl ether, ethylene glycol monobenzyl ether, diethylene glycol monomethyl ether, diethylene glycol monoethyl ether, diethylene glycol monobutyl ether, diethylene glycol monophenyl ether, diethylene glycol monobenzyl ether, triethylene glycol monomethyl ether, triethylene glycol monoethyl ether, triethylene glycol monobutyl ether, triethylene glycol monophenyl ether, triethylene glycol monobenzyl ether and like ethylene oxide adducts; propylene glycol monomethyl ether, propylene glycol monoethyl ether, propylene glycol monobutyl ether, propylene glycol monophenyl ether, propylene glycol monobenzyl ether, dipropylene glycol monomethyl ether, dipropylene glycol monoethyl ether, dipropylene glycol monobutyl ether, dipropylene glycol monophenyl ether, dipropylene glycol monobenzyl ether, tripropylene glycol monomethyl ether, tripropylene glycol monoethyl ether, tripropylene glycol monobutyl ether, tripropylene glycol monophenyl ether, tripropylene glycol monobenzyl ether and like propylene oxide adducts; etc.

Among these, diethylene glycol monomethyl ether, diethylene glycol monoethyl ether, diethylene glycol monobutyl ether, triethylene glycol monomethyl ether, triethylene glycol monoethyl ether, triethylene glycol monobutyl ether and the like are preferable, and diethylene glycol monomethyl ether, diethylene glycol monoethyl ether, diethylene glycol monobutyl ether are especially preferable.

Specific compounds obtainable by the reaction between such dibasic acids and alcohols and/or ether alcohols are, for example, methyl diglycol ethyldiglycol adipate, methyl diglycol butyldiglycol adipate, ethyldiglycol butyldiglycol adipate, benzyl methyl diglycol adipate, benzyl ethyldiglycol adipate, benzyl butyldiglycol adipate, methyl diglycol ethyldiglycol succinate, methyl diglycol butyldiglycol succinate, ethyldiglycol butyldiglycol succinate, benzyl methyl diglycol succinate, benzyl ethyldiglycol succinate, benzyl butyldiglycol succinate and like diglycol esters;

methyl dipropylene glycol ethyl dipropylene glycol adipate, methyl dipropylene glycol butyl dipropylene glycol adipate, ethyl dipropylene glycol butyl dipropylene glycol adipate, benzyl methyl dipropylene glycol adipate, benzyl ethyl dipropylene glycol adipate, benzyl butyl dipropylene glycol adipate, methyl dipropylene glycol ethyl dipropylene glycol succinate, methyl dipropylene glycol butyl dipropylene glycol succinate, ethyl dipropylene glycol butyl dipropylene glycol succinate, benzyl methyl dipropylene glycol succinate, benzyl ethyl dipropylene glycol succinate, benzyl butyl dipropylene glycol succinate and like dipropylene glycol esters; etc.

Among these, diglycol esters are preferable, and methyl diglycol ethyldiglycol adipate, methyl diglycol butyldiglycol adipate, ethyldiglycol butyldiglycol adipate, benzyl methyl diglycol adipate, benzyl ethyldiglycol adipate, benzyl butyldiglycol adipate, methyl diglycol ethyldiglycol succinate, methyl diglycol butyldiglycol succinate, ethyldiglycol butyldiglycol succinate, benzyl methyl diglycol succinate, benzyl ethyldiglycol succinate, benzyl butyldiglycol succinate are especially preferable.

Particularly preferable are methyl diglycol butyldiglycol adipate, benzyl methyl diglycol adipate, benzyl butyldiglycol adipate, methyl diglycol butyldiglycol succinate, benzyl methyl diglycol succinate, benzyl butyldiglycol succinate, and the most preferable are methyl diglycol butyldiglycol adipate, benzyl methyl diglycol adipate and benzyl butyldiglycol adipate.

Citric Acid Ester (B2)

The citric acid ester (B2) is a compound represented by formula (3)

wherein $R^5$ is H, a $C_{15}$ aliphatic acyl group or a $C_{6-12}$ aromatic acyl group, and $R^6$, $R^7$ and $R^8$ are not all the same and each represents a group of formula (4) or (5)

wherein $R^9$ is a $C_{1-6}$ alkylene group, $R^{10}$ is a $C_{1-10}$ straight- or branched-chain alkyl group, a $C_{6-12}$ aryl group, a $C_{7-15}$ arylalkyl group or a $C_{7-15}$ alkylaryl group, and p is an integer from 0 to 6; and wherein $R^{11}$ is a $C_{1-6}$ alkylene group; $R^{12}$ is a $C_{1-10}$ straight- or branched-chain alkyl group, a $C_{6-12}$ aryl group, a $C_{7-15}$ arylalkyl group or a $C_{7-15}$ alkylaryl group; and q is an integer from 0 to 6.

As stated above, $R^5$ is a hydrogen atom, a $C_{15}$ aliphatic acyl group or a $C_{6-12}$ aromatic acyl group. $R^5$ is preferably a $C_{2-4}$ aliphatic acyl group or a $C_{7-10}$ aromatic acyl group, and especially preferably an acetyl group or benzoyl group.

$R^9$ and $R^{11}$ are each a $C_{1-6}$ alkylene group, preferably an ethylene, propylene or butylene group; and especially preferably an ethylene group.

$R^{10}$ and $R^{12}$ are each a $C_{1-10}$ straight- or branched-chain alkyl group, a $C_{6-12}$ aryl group, a $C_{7-15}$ arylalkyl group or a $C_{7-15}$ alkylaryl group; and preferably a $C_{2-8}$ straight- or branched-chain alkyl group, a $C_{6-10}$ aryl group, a $C_{7-10}$ arylalkyl group or a $C_{7-10}$ alkylaryl group. Examples of $R^{10}$ and $R^{12}$ include methyl, ethyl, propyl, butyl, pentyl, hexyl, heptyl, octyl, benzyl and like groups; among which ethyl, propyl, butyl and like groups are preferable, with ethyl and butyl groups being especially preferable. p and q are each an integer from 0 to 6, and preferably an integer from 0 to 4.

Specific examples of the citric acid ester compound (B2) include methoxycarbonyl methyl dimethyl citrate, methoxycarbonyl methyl diethyl citrate, methoxycarbonyl methyl dibutyl citrate, ethoxycarbonyl methyl dimethyl citrate, ethoxycarbonyl methyl dibutyl citrate, ethoxycarbonyl methyl dioctyl citrate, butoxycarbonyl methyl dimethyl citrate, butoxycarbonyl methyl diethyl citrate, butoxycarbonyl methyl dibutyl citrate, dimethoxycarbonyl methyl monomethyl citrate, dimethoxycarbonyl methyl monoethyl citrate, dimethoxycarbonyl methyl monobutyl citrate, diethoxycarbonyl methyl monomethyl citrate, diethoxycarbonyl methyl monobutyl citrate, diethoxycarbonyl methyl monooctyl citrate, dibutoxycarbonyl methyl monomethyl citrate, dibutoxycarbonyl methyl monoethyl citrate, dibutoxycarbonyl methyl monobutyl citrate, and such compounds of formula (3) wherein $R^5$ is acetylated.

Among them, methoxycarbonyl methyl dibutyl citrate, ethoxycarbonyl methyl dibutyl citrate, butoxycarbonyl methyl dibutyl citrate, dimethoxycarbonyl methyl monobutyl citrate, diethoxycarbonyl methyl monobutyl citrate, dibutoxycarbonyl methyl monobutyl citrate and the like are preferable, methoxycarbonyl methyl dibutyl citrate, ethoxycarbonyl methyl dibutyl citrate and butoxycarbonyl methyl dibutyl citrate are especially preferable, and ethoxycarbonyl methyl dibutyl citrate is most preferable.

Number Average Molecular Weight

The number average molecular weight of the mixed alcohol ester is not limited. Generally, the lower the molecular weight, the greater the plasticizing effect but the lower the stability and the higher the possibility of occurrence of blocking or stains caused by bleed-out to the surface of the molded article. Therefore, the mixed alcohol ester preferably has a number average molecular weight of about 200 to about 1500, and more preferably about 300 to about 1000.

Use

The mixed alcohol ester of the present invention is biodegradable and highly compatible with aliphatic polyester resins, and therefore can be suitably used as a plasticizer for biodegradable aliphatic polyester resins.

(II) Biodegradable Resin Composition

Basic Structure

The biodegradable resin composition of the present invention comprises a biodegradable aliphatic polyester resin (A) and a plasticizer (B) comprising an ester of an aliphatic polybasic acid with at least two members selected from the group consisting of alcohols and ether alcohols (i.e., the mixed alcohol ester of the present invention).

Biodegradable Aliphatic Polyester Resin (A)

Examples of the biodegradable aliphatic polyester resin (A) include a polymer (A1) obtainable by dehydration polycondensation of a hydroxycarboxylic acid or acids; an aliphatic polyester (A2) synthesized using an aliphatic dicarboxylic acid or acids and an aliphatic diol or diol or diols as the main components; and a terpolymer (A3) of a hydroxycarboxylic acid, an aliphatic dicarboxylic acid and an aliphatic diol. In the present invention, an aliphatic-aromatic polyester (A4) synthesized from an aliphatic dicarboxylic acid or acids, an aromatic dicarboxylic acid or acids, and an aliphatic diol or diols is also encompassed by the aliphatic polyester resin.

Any combination of the resins (A1) to (A4) may be used as the biodegradable aliphatic polyester resin in the present invention. In particular, the polymer (A1), polymer (A2) or a mixture thereof is preferable, with the polymer (A1) being especially preferable.

<Polymer (A1) of Hydroxycarboxylic Acid>

Hydroxycarboxylic acids usable as starting materials for the polymer (A1) include, for example, glycolic acid, lactic acid, β-hydroxypropionic acid, β-hydroxybutyric acid, hydroxyvaleric acid, hydroxypivalic acid and the like. When such compounds have optical isomers, any of D- and L-isomers and racemates can be used. These compounds are subjected to dehydration polycondensation to obtain high polymers.

The polymer (A1) includes polymers obtainable by transesterification of esters derived from hydroxycarboxylic acids, and polymers (polylactones) obtainable by ring-opening polymerization of cyclic esters (lactones) derived from hydroxycarboxylic acids. Examples of polylactones include "Celgreen" (Daicel Chemical Industries, Ltd.), "Tone Polymer" (Union Carbide Corp.), "CAPA" (Solvay), etc.

The polymer (A1) is preferably a polyhydroxypropionic acid, polyhydroxybutyric acid, poly(lactic acid) or polycaprolactone, and especially preferably a poly(lactic acid) or polycaprolactone.

<<Poly(Lactic Acid)>>

A detailed description of poly(lactic acid)s will be given. Examples of starting materials for poly(lactic acid)s include L-lactic acid, D-lactic acid, DL-lactic acid, their mixtures and lactides, i.e., cyclic dimers of lactic acid. Lactic acids are useful biodegradable aliphatic polyester resins because they can be obtained by fermenting renewable resources such as sugar, starch, etc.

The process for producing the poly(lactic acid) for use in the present invention is not limited. For example, the poly (lactic acid) may be produced by performing direct dehydration condensation of a lactic acid; or by synthesizing a lactide (a cyclic dimer) from a lactic acid and then performing ring-opening polymerization to obtain a high molecular weight poly(lactic acid); or by carrying out ring-opening polymerization of a lactic acid and a cyclic dimer of an aliphatic hydroxycarboxylic acid (for example, a lactide or glycolide and ε-caprolactone) in the presence of a catalyst; or like process.

The lactic acid may be copolymerized with other hydroxycarboxylic acids, aliphatic polyhydric alcohols, aliphatic polybasic acids or the like in an amount that does not impair the properties of the poly(lactic acid). Further, a small amount of chain extender (e.g., a diisocyanate compound, epoxy compound, acid anhydride, etc.) can be used to increase the molecular weight.

The weight average molecular weight (Mw) of the poly (lactic acid) is preferably about 10000 to about 1000000, more preferably about 30000 to about 600000, and even more preferably about 50000 to about 400000. Poly(lactic acid)s with a weight average molecular weight (Mw) within the above ranges have sufficient mechanical strength and excellent processability.

Specific examples of poly(lactic acid)s include "LACTY" (Shimadzu Corp.), "Lacea" (Mitsui Chemicals, Inc.), "Terramac" (Unitika, Ltd.), "Ecologe" (Mitsubishi Plastics, Inc.), "CPLA (tentative name)" (Dainippon Ink & Chemicals, Inc.), "eco-PLA" (Cargill-Dow LLC (U.S.)), "Lactron" (Kanebo Gohsen, Ltd.), etc.

<Aliphatic Polyester (A2)>

The aliphatic polyester (A2), synthesized using an aliphatic dicarboxylic acid and aliphatic diol as the main components, is produced from various combinations of aliphatic dicarboxylic acids and aliphatic diols and is not limited as long as it is biodegradable.

Examples of aliphatic dihydric alcohols for use as a material of the aliphatic polyester (A2) include ethylene glycol, diethylene glycol, triethylene glycol, polyethylene glycol, propylene glycol, dipropylene glycol, 1,3-butanediol, 1,4-butanediol, 1,6-hexanediol, 1,9-nonanediol, neopentylglycol, 1,4-cyclohexanedimethanol, 1,4-benzenedimethanol and the like. Among these, ethylene glycol and 1,4-butanediol are preferable, with 1,4-butanediol being especially preferable. Aliphatic dihydric alcohols can be used singly or in combination.

Examples of aliphatic dicarboxylic acids usable as the other main component of the aliphatic polyester (A2) include succinic acid, oxalic acid, malonic acid, glutaric acid, adipic acid, pimelic acid, suberic acid, azelaic acid, sebacic acid and the like. Among these, succinic acid and adipic acid are preferable. Aliphatic dicarboxylic acids can be used singly or in combination.

The aliphatic polyester (A2) may be synthesized using, in addition to aliphatic dicarboxylic acids and aliphatic diols, a third polymerization component such as an aliphatic hydroxycarboxylic acid in an amount that does not impair the physical properties (e.g., flexibility) or biodegradability of the resin.

Examples of polymerizable aliphatic hydroxycarboxylic acids include lactic acid, glycolic acid, hydroxybutyric acid, 4-hydroxybutyric acid, 3-hydroxyvaleric acid, 4-hydroxyvaleric acid, 6-hydroxycaproic acid and the like. When such compounds have optical isomers, any of D- and L-isomers and racemates can be used. Cyclic esters of aliphatic hydroxycarboxylic acids, such as ε-caprolactone, are also usable. The polymerizable aliphatic hydroxycarboxylic acids can used singly or in combination.

The aliphatic polyester (A2) can be produced by carrying out direct polymerization of the above components to obtain a high polymer, or by performing indirect polymerization in which the above components are polymerized to form an oligomer, which is then converted to a high polymer with a chain extender or the like. Specifically, in direct polymerization, a high polymer is usually obtained while removing water from the starting compounds or generated during the polymerization. In indirect polymerization, after polymerizing the selected starting materials to form an oligomer, a small amount of chain extender (e.g., a diisocyanate compound such as hexamethylene diisocyanate, isophorone diisocyanate, xylylene diisocyanate or diphenylmethane diisocyanate) is used to increase the molecular weight, or a carbonate compound is used to obtain a high-molecular-weight aliphatic polyester carbonate. Any of these processes can be used in the present invention.

The aliphatic polyester (A2) may be a modified aliphatic polyester obtained by co-condensation with terephthalic acid, carbonate or the like.

Specific examples of modified aliphatic polyesters obtained by co-condensation with terephthalic acid include "Ecoflex" (BASF), "Easter Bio" (Eastman Chemical Company), "Biomax" (DuPONT) and the like. Examples of modified aliphatic polyesters obtained by co-condensation with carbonate include "IUPEC" (Mitsubishi Gas Chemical Co., Inc.) and the like.

Specific examples of aliphatic polyesters (A2) include polyethylene succinate, polybutylene succinate, polybutylene succinate adipate, polyhexamethylene succinate, polyethylene adipate, polybutylene adipate, polyhexamethylene adipate, polyethylene oxalate, polybutylene oxalate, polyhexamethylene oxalate, polyethylene sebacate, polybutylene sebacate, polyhexamethylene sebacate and the like. These can be used singly or in combination.

From the viewpoint of commercial availability and properties (melting point, biodegradability) of the resulting polymer, polyethylene succinate, polybutylene succinate and polybutylene succinate adipate are preferable, with polybutylene succinate and polybutylene succinate adipate being especially preferable.

Specific examples of polybutylene succinate include "Bionolle" (Showa High Polymer Co., Ltd.), "GS-Pla" (Mitsubishi Chemical Corp.), "SKYGREEN" (SK Chemicals) and the like. Specific examples of polybutylene succinate adipate include "Bionolle" (Showa High Polymer Co., Ltd.) and the like. Specific examples of polyethylene succinate include "Lunare" (Nippon Shokubai Co., Ltd.) and the like.

The weight average molecular weight of the aliphatic polyester (A2) used in the present invention is not limited as long as the polyester has mechanical properties sufficient for practical use. Generally, the weight average molecular weight is preferably about 10000 to about 1000000, more preferably about 30000 to about 500000, and even more preferably about 50000 to about 300000. An aliphatic polyester with a molecular weight within the above range has sufficient mechanical strength and excellent molding processability, i.e., it is easy to handle.

Further, the aliphatic polyester (A2) preferably has a melting point of about 70 to about 200° C., more preferably about 80 to about 160° C. An aliphatic polyester (A2) with a melting point within the above range has good heat resistance, and it is easy to produce the aliphatic polyester (A2).

<Terpolymer (A3)>

As described above, a terpolymer (A3) of a hydroxycarboxylic acid, an aliphatic dicarboxylic acid and an aliphatic diol can also be used as the aliphatic polyester resin in the present invention.

The hydroxycarboxylic acid, aliphatic dicarboxylic acid and aliphatic diol are not limited and may be those shown as the starting materials for the polymers (A1) and (A2). Preferred combinations of a hydroxycarboxylic acid, aliphatic dicarboxylic acid and aliphatic diol are, for example, lactic acid/succinic acid/ethylene glycol, lactic acid/succinic acid/1,4-butanediol, lactic acid/adipic acid/ethylene glycol, and lactic acid/adipic acid/1,4-butanediol.

The weight average molecular weight of the terpolymer (A3) is not limited as long as the terpolymer has mechanical properties sufficient for practical use.

<Aliphatic-Aromatic Polyester (A4)>

As stated above, the aliphatic polyester resin (A) encompasses polyesters of aliphatic dicarboxylic acids, aromatic dicarboxylic acids and aliphatic diols.

The aliphatic dicarboxylic acids and aliphatic diols are not limited and may be those shown as the starting materials for the polymer (A2). The aromatic dicarboxylic acids are not limited, and known compounds such as (ortho)phthalic acid, isophthalic acid, terephthalic acid and naphthalene dicarboxylic acid are usable.

Preferred combinations of an aliphatic dicarboxylic acid, aromatic dicarboxylic acid and aliphatic diol include succinic acid/terephthalic acid/butanediol, succinic acid/terephthalic acid/ethylene glycol, succinic acid/isophthalic acid/butanediol, succinic acid/isophthalic acid/ethylene glycol, adipic acid/terephthalic acid/butanediol, adipic acid/terephthalic acid/ethylene glycol, adipic acid/isophthalic acid/butanediol, and adipic acid/isophthalic acid/ethylene glycol. Particularly preferred is the combination of adipic acid/terephthalic acid/butanediol.

The copolymerization ratio (molar ratio) of the aliphatic dicarboxylic acid/aromatic dicarboxylic acid is preferably about 1/0.02 to about 1/5, and more preferably about 1/0.05 to about 1/2.

Specific examples of the polyester (A4) of an aliphatic dicarboxylic acid, aromatic dicarboxylic acid and aliphatic diol include "Ecoflex" (BASF), "Easter Bio" (Eastman Chemical Company), "Biomax" (DuPONT) and the like.

The weight average molecular weight of the polyester (A4) is not limited as long as the polyester has mechanical properties sufficient for practical use.

Mixed Alcohol Ester Plasticizer (B)

A plasticizer comprising the mixed alcohol ester of the present invention can be used as the mixed alcohol ester plasticizer (B).

A preferred amount of the mixed alcohol ester plasticizer to be added is about 3 to about 50 parts by weight, particularly about 5 to about 40 parts by weight, and more particularly about 8 to about 30 parts by weight, relative to 100 parts by weight of the aliphatic polyester resin (A). The plasticizer, when added in an amount within the above ranges, exhibits a sufficient plasticizing effect and is unlikely to or does not bleed out.

Other Components

The biodegradable resin composition of the present invention may contain, where necessary, other components that are often used in biodegradable resin compositions, in such an amount that does not impair the effects of the present invention. Such components include modifiers, crystal nucleating agents, perfumes, antimicrobial agents, pigments, dyes, heat-resistant materials, antioxidants, weather-proofing agents, lubricants, antistatic agents, stabilizers, fillers, reinforcing agents, anti-blocking agents, flame retardants, other plasticizers, other polymers (e.g., thermoplastic resins such as polyethylene, polypropylene, polystyrene, polyvinyl chloride, polyethylene terephthalate, polybutylene terephthalate, polycarbonate and polyamide), wood flours, starches, etc.

The mixed alcohol ester of the present invention performs sufficiently well as a plasticizer even when used singly, but can also be used in combination with other plasticizers. Known plasticizers for biodegradable aliphatic polyester resins can be used as such other plasticizers, without limitation. Such known plasticizers include dibasic acid esters, citric acid esters, polyalkylene glycol diesters, polyhydric alcohol esters, polyester plasticizers, polyether ester plasticizers, etc.

Production Process

The plasticizer (B) may be added to the polymerization materials for the biodegradable aliphatic polyester resin (A), added during the polymerization process for the polyester resin (A), or mixed after the polymerization of the polyester resin (A). However, when the plasticizer is added to the polymerization materials or added during the polymerization process, the plasticizer (B) may degrade or copolymerize with the polyester resin (A) by transesterification, thereby failing to properly achieve the desired plasticizing effect. Therefore, it is preferable that the plasticizer (B) be mixed after the polymerization of the polyester resin (A) and before or during the molding process.

The method and apparatus for mixing the polyester resin (A) and mixed alcohol ester plasticizer (B) are not limited, and may be a known method and apparatus. In particular, methods and apparatus that enable continuous processing are industrially advantageous and preferable. For example, the polyester resin (A) and plasticizer (B) may be mixed at a predetermined ratio, placed in the hopper of an extruder, melted and immediately extruded. Alternatively, the polyester resin (A) and plasticizer (B), after being melted and mixed, may be palletized and then melted and molded as necessary. The latter method including pelletization is preferable in order to homogeneously mix the polyester resin (A) with the mixed alcohol ester plasticizer (B).

In these melting and mixing methods, it is desirable to substantially prevent degradation and change in properties of the polymers, and for that purpose it is preferable to carry out mixing at the lowest possible temperature and within the shortest possible period. The melt extrusion temperature may be selected considering the melting point of the resin used, and the mixing ratio of the resin (A) and plasticizer (B), etc. and is usually about 100 to about 250° C.

(III) Method for Plasticizing Biodegradable Aliphatic Polyester Resin

The method for plasticizing a biodegradable aliphatic polyester resin according to the present invention comprises adding a compound represented by formula (1) or (3) to a biodegradable aliphatic polyester resin. The biodegradable aliphatic polyester resin (A) can be used as the biodegradable aliphatic polyester resin in this method.

A preferred amount of the mixed alcohol ester to be added is usually about 3 to about 50 parts by weight, particularly about 5 to about 40 parts by weight, and more particularly about 8 to about 30 parts by weight, relative to 100 parts by weight of the aliphatic polyester resin (A). The mixed alcohol ester, when added in an amount within the above ranges, shows a sufficient plasticizing effect and is unlikely to or does not bleed out.

EXAMPLES

The following Examples, Comparative Examples and Test Examples further illustrate the present invention and are not intended to limit the scope of the invention.

1. Components

In the Examples and Comparative Examples, the following components were used.

1) Aliphatic Polyester Resin (A)

Poly(lactic acid): "LACTY9030" manufactured by Shimadzu Corp.
(Hydroxycarboxylic acid polymer (A1))

Aliphatic polyester: "Bionolle #3020" manufactured by Showa High Polymer Co., Ltd. (Aliphatic polyester (A2))

2) Mixed Alcohol Ester Plasticizer (B)

Methyl diglycol butyldiglycol adipate: Mixed alcohol ester 1

Benzyl butyldiglycol adipate: Mixed alcohol ester 2

Benzyl methyl diglycol adipate: Mixed alcohol ester 3

Ethoxycarbonyl methyldibutyl citrate: Mixed alcohol ester 4

3) Single Alcohol Ester Plasticizer (Used in Comparative Examples)

Bis(butyldiglycol) adipate: Single alcohol ester 1 "BXA" manufactured by Daihachi Chemical Industry Co., Ltd.

Bis(methyl diglycol) adipate: Single alcohol ester 2 "MXA" manufactured by Daihachi Chemical Industry Co., Ltd.

Dibenzyl adipate: Single alcohol ester 3

Triethoxycarbonyl methyl citrate: Single alcohol ester 4

Tributyl citrate (TBC): Single alcohol ester 5

2. SYNTHESIS EXAMPLES

Synthesis Example 1

Synthesis of Mixed Alcohol Ester 1

A 1 L four-necked flask equipped with a stirrer, thermometer, water separator and reflux tube was charged with 146.0 g (1.0 mole) of adipic acid, 120.0 g (1.0 mole) of diethylene glycol monomethyl ether, 178.2 g (1.1 moles) of diethylene glycol monobutyl ether, 1.9 g of p-toluenesulfonic acid and 120.0 g of toluene. The mixture was heated to 118° C. over a period of 30 minutes while being stirred at atmospheric pressure. Reflux started at the above temperature (118° C.). Six hours after the start of refluxing, the temperature rose to 145° C. due to the generation of esters and 37.3 g (2.1 moles) of water was recovered. Since no more water generation was observed, the reaction was judged to be complete. After the completion of the reaction, the reaction product was cooled to 60° C. and neutralized by adding, at the same temperature (60° C.), sodium carbonate in an amount corresponding to twice the acid value of the reaction product (2.4 g in Synthesis Example 1) and 120.0 g of water. Thereafter, the organic layer was washed with 120.0 g of water and heated to 120° C. Toluene was recovered until the pressure reached about 4 kPa. Subsequently, steam distillation was performed at the same pressure at 120° C. for 1 hour to remove low-boiling components from the reaction product, and thereby 380.5 g of a colorless transparent liquid was obtained. The yield was 96.9% and the acid value of the product was 0.09 (mg KOH/g).

Figure 1:
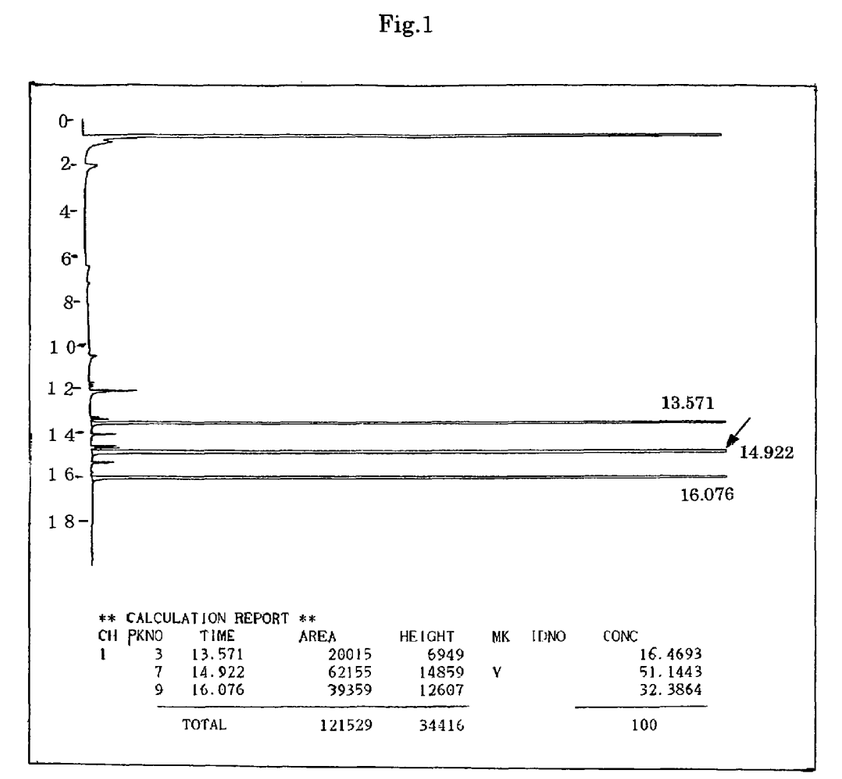
FIG. 1 is a gas chromatogram of the product obtained in Synthesis Example 1.

Gas chromatographic analysis of the product was carried out under the conditions listed below, and found that the purity of the desired product, i.e., methyl diglycol butyldiglycol adipate, was 51.1% by area. FIG. 1 shows the results of the gas chromatographic analysis. In FIG. 1, the arrow indicates the peak attributed to methyl diglycol butyldiglycol adipate.

<Gas Chromatography Conditions>
Instrument:
  GC-17A manufactured by Shimadzu Corp.
Column:
  DB-1 (manufactured by J&W,
  100% dimethylpolysiloxane)
  0.32 mm (diameter)×30 m, 0.25 μm film thickness
Detector: FID
Carrier gas: He Synthesis Example 2

Synthesis of Mixed Alcohol Ester 2

The procedure of Synthesis Example 1 was followed except for using as alcohol materials 108.0 g (1.0 mole) of benzyl alcohol and 166.3 g (1.03 moles) of diethylene glycol monobutyl ether. As a result, 369.5 g of a colorless transparent liquid was obtained. The yield was 97.1% and the acid value of the product was 0.08 (mg KOH/g).

Figure 2:
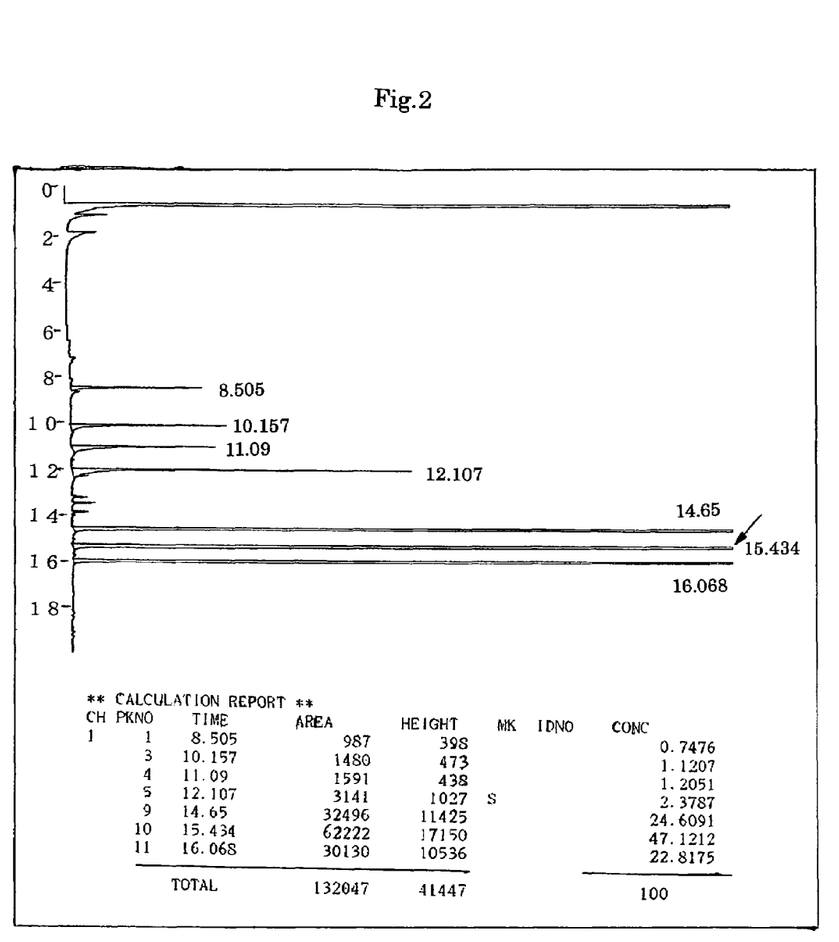
FIG. 2 is a gas chromatogram of the product obtained in Synthesis Example 2.

Gas chromatographic analysis of the product was carried out under the same conditions as in Synthesis Example 1, and found that the purity of the desired product, benzyl butyldiglycol adipate, was 47.1% by area. FIG. 2 shows the results of the gas chromatographic analysis. In FIG. 2, the arrow indicates the peak attributed to benzyl butyldiglycol adipate.

Synthesis Example 3

Synthesis of Mixed Alcohol Ester 3

The procedure of Synthesis Example 1 was followed except for using 114.9 g (1.06 moles) of benzyl alcohol in place of 178.2 g (1.1 moles) of diethylene glycol monobutyl ether. As a result, 323.0 g of a colorless transparent liquid was obtained. The yield was 85.0% and the acid value of the product was 0.09 (mg KOH/g).

Figure 3:
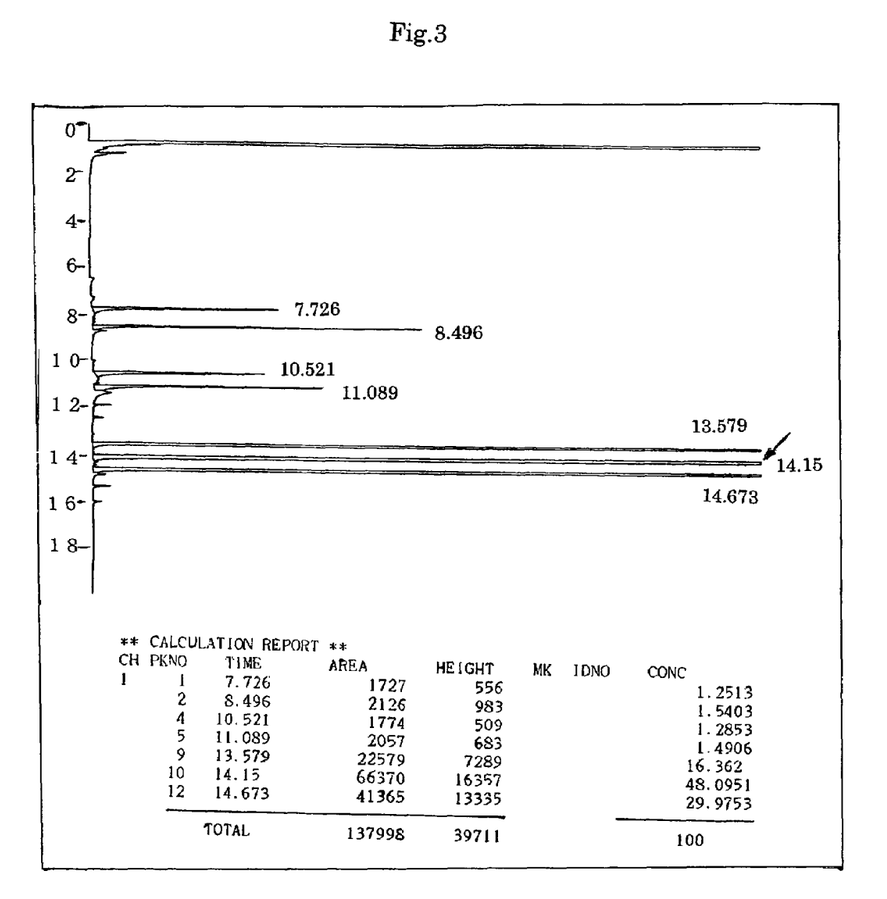
FIG. 3 is a gas chromatogram of the product obtained in Synthesis Example 3.

Gas chromatographic analysis of the product was carried out under the same conditions as in Synthesis Example 1, and found that the purity of the desired product, benzyl methyl diglycol adipate, was 48.1% by area. FIG. 3 shows the results of the gas chromatographic analysis. In FIG. 3, the arrow indicates the peak attributed to benzyl methyl diglycol adipate.

Synthesis Example 4

Synthesis of Mixed Alcohol Ester 4

A 1 L four-necked flask equipped with a stirrer, thermometer and reflux tube was charged with 192.0 g (1.0 mole) of anhydrous citric acid and 148.0 g (2.0 moles) of butanol. The mixture was heated to 110° C. over a period of 30 minutes while being stirred at atmospheric pressure, and reacted to reach a reaction temperature of 115° C. over 6 hours. The reaction product was cooled to 60° C. and neutralized by slowly adding, at the same temperature (60° C.), a mixture of sodium carbonate in an amount corresponding to twice the acid value of the reaction product (i.e., 80.0 g) and 170.0 g of water. Dehydration was then carried out at atmospheric pressure, and 100 g of water was thereby recovered. Subsequently, a water separator was attached to the flask, and 147.0 g (1.2 moles) of ethyl monochloroacetate, 1.0 g of triethylamine and 100.0 g of toluene were added to the flask. The mixture was heated to 100° C. over a period of 30 minutes while being stirred under a reduced pressure of about 67 kPa. Ten hours after the start of the reaction, 124.0 g of water had been recovered and the reaction was completed. After the completion of the reaction, the reaction product was cooled to 40° C., 340.0 g of a 1% aqueous hydrochloric acid solution was added, and the sodium chloride and quaternary ammonium salt of triethylamine formed as by-products were removed. Subsequently, the organic layer was neutralized by adding sodium carbonate in an amount corresponding to twice the acid value of the organic layer (i.e., 5.0 g) and 340.0 g of water. Subsequently, the organic layer was washed with 340.0 g of water and heated to 120° C., toluene was recovered until the pressure reached about 4 kPa, and steam distillation was carried out at the same pressure at 120° C. for 1 hour to remove low-boiling components from the reaction product. As a result, 270.0 g of a reddish-yellow transparent liquid was obtained. The yield was 69.1% and the acid value of the product was 0.025 (mg KOH/g).

Figure 4:
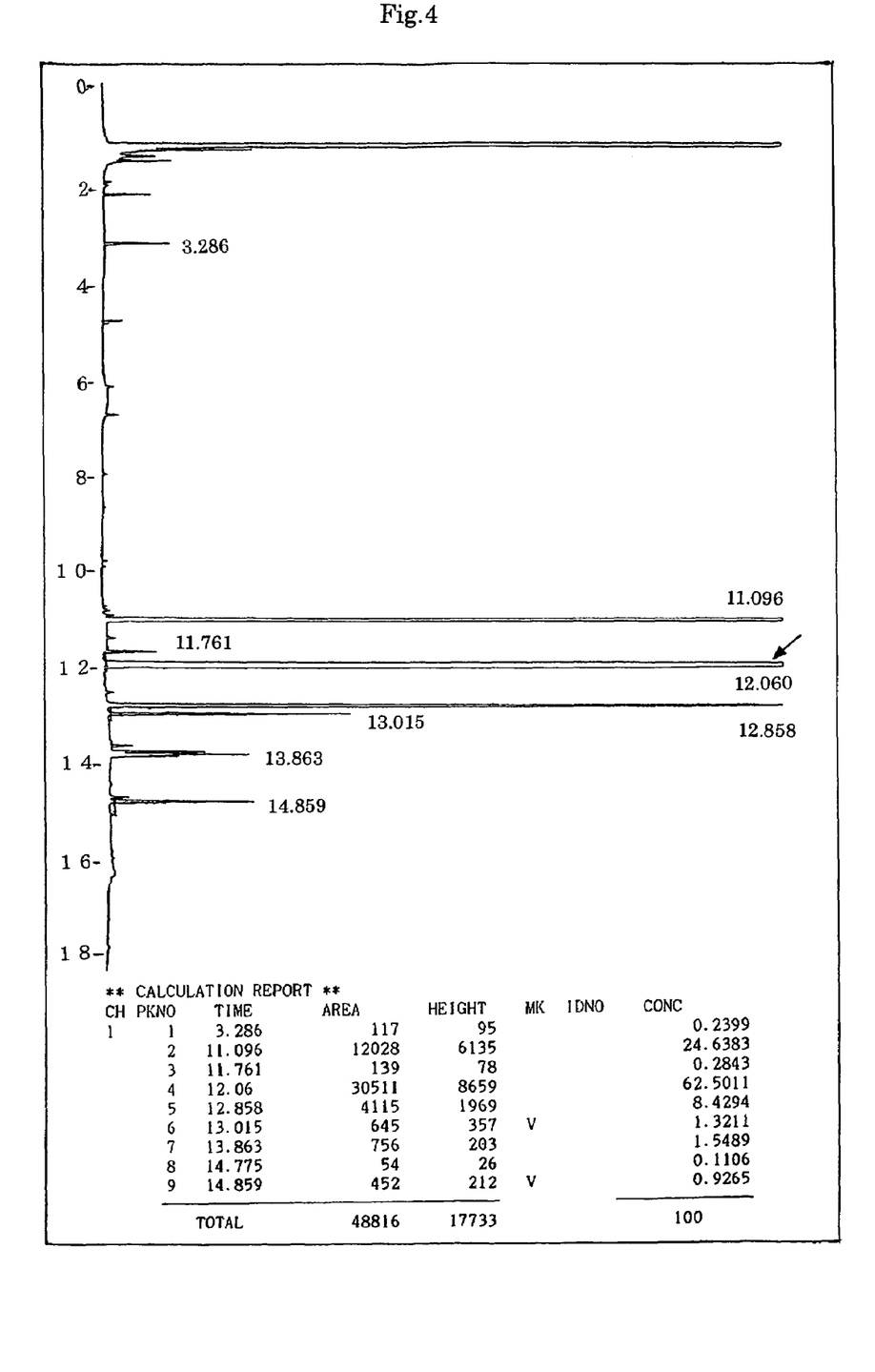
FIG. 4 is a gas chromatogram of the product obtained in Synthesis Example 4.

Gas chromatographic analysis of the product was carried out under the same conditions as in Synthesis Example 1, and found that the purity of the desired product, ethoxycarbonyl methyl dibutyl citrate, was 62.5% by area. FIG. 4 shows the results of the gas chromatographic analysis. In FIG. 4, the arrow indicates the peak attributed to ethoxycarbonyl methyl dibutyl citrate.

Reference Synthesis Example 1

Synthesis of Single Alcohol Ester 3

A 1 L four-necked flask equipped with a stirrer, thermometer, water separator and reflux tube was charged with 146.0 g (1.0 mole) of adipic acid, 237.6 g (2.2 moles) of benzyl alcohol, 1.9 g of p-toluenesulfonic acid and 100.0 g of toluene, and the mixture was heated to 95° C. over a period of 20 minutes while being stirred under a reduced pressure of about 67 kPa. Reflux started at the above temperature (95° C.). Six hours after the start of refluxing, the temperature rose to 125° C. due to the generation of esters and 36.0 g (2.0 moles) of water was recovered. Since no more water generation was observed, the reaction was judged to be complete. After the completion of the reaction, the reaction product was treated in the same manner as in Synthesis Example 1. Thus, 319.2 g of a colorless transparent liquid was obtained. The yield was 97.8% and the acid value of the product was 0.09 (mg KOH/g).

Reference Synthesis Example 2

Synthesis of Single Alcohol Ester 4

A 1 L four-necked flask equipped with a stirrer, thermometer, water separator and reflux tube was charged with 294.1 g (1.0 mole) of trisodium citrate dihydrate, 404.3 g (3.3 moles) of ethyl monochloroacetate, 0.3 g of triethylamine and 77.5 g of toluene, and the mixture was heated to 110° C. over a period of 30 minutes while being stirred under a reduced pressure of about 53 kPa. Toluene started to reflux at the same temperature (110° C.), and after the refluxing reached a stable state, 11.8 g of triethylamine was added over a period of 10 hours. Sixteen hours after the start of the reaction, 36.0 g (2.0 moles) of crystal water of trisodium citrate dihydrate had been recovered. Since no more water generation was observed, the reaction mixture was stirred at the same temperature and pressure for 1 hour, and the reaction was judged to be complete. After the reaction was complete, the reaction mixture was cooled to 40° C., 560.0 g of a 1% aqueous hydrochloric acid solution was added, and the sodium chloride and quaternary ammonium salt of triethylamine generated as by-products were removed. Subsequently, the organic layer was neutralized by adding sodium carbonate in an amount corresponding to twice the acid value of the organic layer (14.2 g) and 185.0 g of water. Subsequently, the organic layer was washed with 185.0 g of water and then heated to 120° C. Toluene was recovered until the pressure reached about 5 kPa, and steam distillation was performed at the same pressure for 1 hour to remove low-boiling components from the reaction product. Thus, 412.4 g of a reddish yellow transparent liquid was obtained. The yield was 91.5% and the acid value of the product was 0.126 (mg KOH/g).

Reference Synthesis Example 3

Synthesis of Single Alcohol Ester 5

A 1 L four-necked flask equipped with a stirrer, thermometer, condenser and distillate receiver was charged with 192.0 g (1.0 mole) of anhydrous citric acid, 267.0 g (3.6 moles) of butanol and 1.9 g of sulfuric acid. The mixture was heated to 95° C. over a period of 20 minutes while being stirred at atmospheric pressure. While recovering butanol and water generated as by-products of esterification in the receiver, stirring was continued for 3 hours until the reaction temperature reached 105° C. Subsequently, while recovering butanol and water generated as by-products of esterification in the receiver, 222.0 g (3.0 moles) of additional butanol was added at a reaction temperature of 101 to 143° C. over a period of 3 hours to complete the reaction. After the completion of the reaction, the reaction product was cooled to 60° C., and at the same temperature (60° C.), neutralized by adding sodium carbonate in an amount corresponding to twice the acid value of the reaction product (i.e., 2.0 g) and 120.0 g of water. Subsequently, the organic layer was washed with 120.0 g of water and heated to 120° C. Excess butanol was recovered until the pressure reached about 4 kPa, and steam distillation was performed at the same pressure at 120° C. for 1 hour to remove low-boiling components from the reaction product, to thereby obtain 329.0 g of a colorless transparent liquid. The yield was 94.1% and the acid value of the product was 0.025 (mg KOH/g).

3. Evaluation Methods

1) Preparation of Test Pieces (1) Poly(Lactic Acid)

A plasticizer was added in an amount of 15, 20 or 30 parts by weight relative to 100 parts by weight of a poly(lactic acid). The resulting mixture was mixed at a roll kneading temperature of 160 to 165° C. for 10 minutes and formed into a sheet, which was then compressed in a compression molding machine (heating: 155° C., 150 kg/cm$^2$, 3 min., cooling: 50 kg/cm$^2$, 3 min.) to a thickness of 0.5 mm. Rectangular dumbbell test pieces (JIS K7127/5: test piece type 5) with a width of 25 mm and a length of 115 mm were prepared using the sheet.

(2) Aliphatic Polyester

Using an aliphatic polyester in place of a poly(lactic acid), the above procedure was followed except that a roll temperature of 95 to 100° C. and a heating temperature in the compression molding machine of 95° C. were employed.

2) Bleeding Test

A test piece (3 cm×4 cm) was cut out from the sheet, dried and aged at 80° C. for 24 hours in a constant-temperature oven. Thereafter, the surface condition of the test piece was visually observed to evaluate the non-bleeding properties by the following criteria.
A: No plasticizer bleeding
B: Slight plasticizer bleeding
C: Some plasticizer bleeding 3) Water Resistance Test A test piece (3 cm×4 cm) was cut out from the sheet, weighed and immersed in water at room temperature for 48 hours. The test piece was taken out, thoroughly wiped to remove water, dried in a desiccator containing silica gel for 12 hours, and weighed to evaluate the water resistance from the loss in weight (%) by the following criteria.
A: Less than 0.50% change in weight
B: 0.50 to less than 1.0% change in weight
C: At least 1.0% change in weight 4) Tensile Test The tensile modulus (kgf/cm$^2$) and tensile elongation (%) were measured according to JIS K7127.
Dumbbell width: 6.85 mm
Film thickness: 0.55±0.1 mm
Load cell: 50 kg
Chuck distance: 50 mm
Test speed: 5 mm/min. (poly(lactic acid)) 300 mm/min. (Bionolle)
Test piece type: 5

4. Test Piece Production Examples and Evaluation Results
1) Poly(Lactic Acid)

Example 1

Poly(Lactic Acid)

Test pieces were prepared by the method described above using 20 parts by weight of Mixed alcohol ester 1 as the mixed alcohol ester plasticizer (B) relative to 100 parts by weight of "LACTY 9030" (a poly(lactic acid) manufactured by Shimadzu Corp.) as the aliphatic polyester resin (A).

Example 2

Poly(Lactic Acid)

Test pieces were prepared in the same manner as in Example 1 except for using Mixed alcohol ester 2 in place of Mixed alcohol ester 1.

Example 3

Poly(Lactic Acid)

Test pieces were prepared in the same manner as in Example 1 except for using Mixed alcohol ester 3 in place of Mixed alcohol ester 1.

Example 4

Poly(Lactic Acid)

Test pieces were prepared in the same manner as in Example 1 except for using 30 parts by weight of Mixed alcohol ester 4 as the mixed alcohol ester plasticizer (B).

Comparative Example 1

Test pieces were prepared in the same manner as in Example 1 except that no plasticizer was used.

Comparative Examples 2 to 6

Test pieces were prepared in the same manner as in Example 1 except for using one of Mixed alcohol esters 1 to 5 in place of Mixed alcohol ester 1.

Table 1 shows the compositions of the test pieces prepared in Examples 1 to 3 and Comparative Examples 1 to 4 and test results. Table 2 shows the compositions of the test pieces prepared in Example 4 and Comparative Examples 1, 5 and 6 and test results.

the test pieces prepared in Comparative Examples 2, 3 and 4 in which bis(butyldiglycol) adipate (Single alcohol ester 1), bis(methyl diglycol) adipate (Single alcohol ester 2) and dibenzyl adipate (Single alcohol ester 3), respectively, were used as plasticizers.

The test pieces of Example 3 in which benzyl methyl diglycol adipate (Mixed alcohol ester 3) was used as the mixed alcohol ester plasticizer (B) were excellent in all of non-bleeding properties, water resistance and elongation. These results were superior to those of the test pieces prepared in Comparative Examples 3 and 4 in which bis (methyl diglycol) adipate (Single alcohol ester 2) and dibenzyl adipate (Single alcohol ester 3), respectively, were used as plasticizers.

TABLE 1

|  |  |  | Ex. 1 | Ex. 2 | Ex. 3 | Comp. Ex. 1 | Comp. Ex. 2 | Comp. Ex. 3 | Comp. Ex. 4 |
|---|---|---|---|---|---|---|---|---|---|
| Composition (parts) | (A) Resin component | Poly (lactic acid) | 100 | 100 | 100 | 100 | 100 | 100 | 100 |
|  | (B) Plasticizer component | Mixed alcohol 1 | 20 | — | — | — | — | — | — |
|  |  | Mixed alcohol 2 | — | 20 | — | — | — | — | — |
|  |  | Mixed alcohol 3 | — | — | 20 | — | — | — | — |
|  |  | Single alcohol 1 | — | — | — | — | 20 | — | — |
|  |  | Single alcohol 2 | — | — | — | — | — | 20 | — |
|  |  | Single alcohol 3 | — | — | — | — | — | — | 20 |
| Properties | Non-bleeding properties |  | A | A | A | — | C | A | B |
|  | Water resistance |  | A | A | A | — | C | C | A |
|  | Tensile modulus | Kgf/cm$^2$ | 278 | 456 | 5733 | 24820 | 4926 | 1817 | 3557 |
|  | Elongation | % | >300 | >300 | 275 | 3 | 16 | 23 | 200 |

(Mixed alcohol: Mixed alcohol ester, Single alcohol: Single alcohol ester)

As is apparent from Table 1, the test pieces of Comparative Examples 2, 3 and 4, prepared using single alcohol esters as plasticizers, were not satisfactory in both non-bleeding properties and water resistance. Further, these test pieces had a high tensile modulus and low elongation, demonstrating a poor plasticizing effect.

TABLE 2

|  |  |  | Ex. 4 | Comp. Ex. 1 | Comp. Ex. 5 | Comp. Ex. 6 |
|---|---|---|---|---|---|---|
| Composition (parts) | (A) Resin component | Poly (lactic acid) | 100 | 100 | 100 | 100 |
|  | (B) Plasticizer component | Mixed alcohol 4 | 30 | — | — | — |
|  |  | Single alcohol 4 | — | — | 20 | — |
|  |  | Single alcohol 5 | — | — | — | 20 |
| Properties | Non-bleeding properties |  | A | — | A | C |
|  | Water resistance |  | A | — | A | A |
|  | Tensile modulus | kgf/cm$^2$ | 28 | 24820 | 9257 | 5274 |
|  | Elongation | % | 300 | 3 | 200 | 100 |

(Mixed alcohol: Mixed alcohol ester, Single alcohol: Single alcohol ester)

In contrast, the test pieces of Examples 1 and 2, in which methyl diglycol butyldiglycol adipate (Mixed alcohol ester 1) and benzyl butyldiglycol adipate (Mixed alcohol ester 2), respectively, were used as the mixed alcohol ester plasticizer (B), were excellent in both non-bleeding properties and water resistance. Further, these test pieces had a little tensile modulus and large elongation, demonstrating an excellent plasticizing effect. These results were superior to those of As is apparent from Table 2, the test pieces of Comparative Example 5 prepared using Single alcohol ester 4 as a plasticizer had a large tensile modulus and somewhat little elongation, demonstrating a poor plasticizing effect. Further, the test pieces of Comparative Example 6 prepared using Single alcohol ester 5 as a plasticizer had inferior non-bleeding properties and possessed a large tensile modulus and little elongation, demonstrating a poor plasticizing effect.

In contrast, the test pieces of Example 4 prepared using ethoxycarbonyl methyl dibutyl citrate (Mixed alcohol ester 4) as the mixed alcohol ester plasticizer (B) were excellent in both non-bleeding properties and water resistance, and had a little tensile modulus and large elongation, demonstrating an excellent plasticizing effect.

2) Aliphatic Polyester (A2)

Example 5

Aliphatic Polyester

Test pieces were prepared by the method described above using 15 parts by weight of Mixed alcohol ester 2 as the mixed alcohol ester plastizer (B) relative to 100 parts by weight of "Bionolle #3020" (an aliphatic polyester manufactured by Showa High Polymer Co., Ltd.) as the aliphatic polyester (A).

Example 6

Aliphatic Polyester

Test pieces were prepared in the same manner as in Example 5 except for using Mixed alcohol ester 3 in place of Mixed alcohol ester 2.

Example 7

Aliphatic Polyester

Test pieces were prepared in the same manner as in Example 5 except for using 30 parts by weight of Mixed alcohol ester 4 in place of Mixed alcohol ester 2.

Comparative Example 7

Aliphatic Polyester

Test pieces were prepared in the same manner as in Example 5 except that no plasticizer was used.

Comparative Example 8

Aliphatic Polyester

Test pieces were prepared in the same manner as in Example 5 except for using Single alcohol ester 1 in place of Mixed alcohol ester 2.

Comparative Example 9

Aliphatic Polyester

Test pieces were prepared in the same manner as in Example 5 except for using Single alcohol ester 2 in place of Mixed alcohol ester 2.

Comparative Example 10

Aliphatic Polyester

Test pieces were prepared in the same manner as in Example 5 except for using Single alcohol ester 3 in place of Mixed alcohol ester 2.

Comparative Example 11

Aliphatic Polyester

Test pieces were prepared in the same manner as in Example 5 except for using 30 parts by weight of Single alcohol ester 4 in place of Mixed alcohol ester 2.

Comparative Example 12

Aliphatic Polyester

Test pieces were prepared in the same manner as in Example 5 except for using Single alcohol ester 5 in place of Mixed alcohol ester 2.

Table 3 shows the compositions and test results of the test pieces prepared in Examples 5 and 6 and Comparative Examples 7 to 10. Table 4 shows the compositions and test results of the test pieces prepared in Example 7 and Comparative Examples 7, 11 and 12.

TABLE 3

|  |  |  | Ex. 5 | Ex. 6 | Comp. Ex. 7 | Comp. Ex. 8 | Comp. Ex. 9 | Comp. Ex. 10 |
|---|---|---|---|---|---|---|---|---|
| Composition (parts) | (A) Resin component | Polyester | 100 | 100 | 100 | 100 | 100 | 100 |
|  | (B) Plasticizer component | Mixed alcohol 2 | 15 | — | — | — | — | — |
|  |  | Mixed alcohol 3 | — | 15 | — | — | — | — |
|  |  | Single alcohol 1 | — | — | — | 15 | — | — |
|  |  | Single alcohol 2 | — | — | — | — | 20 | — |
|  |  | Single alcohol 3 | — | — | — | — | — | 15 |
| Properties | Non-bleeding properties |  | A | A | — | B | A | B |
|  | Water resistance |  | A | B | — | C | C | A |
|  | Tensile modulus | kgf/cm$^2$ | 1754 | 1829 | 3640 | 1933 | 1914 | 1895 |
|  | Elongation | % | 250 | 250 | 200 | 300 | 280 | 250 |

(Mixed alcohol: Mixed alcohol ester, Single alcohol: Single alcohol ester)

As is apparent from Table 3, the test pieces of Comparative Examples 8, 9 and 10 prepared using bis(butyldiglycol) adipate (Single alcohol ester 1), bis (methyl diglycol) adipate (Single alcohol ester 2) and dibenzyl adipate (Single alcohol ester 3), respectively, as plasticizers did not satisfactorily achieve both non-bleeding properties and water resistance.

In contrast, the test pieces of Example 5 prepared using benzyl butyldiglycol adipate (Mixed alcohol ester 2) as the mixed alcohol ester plasticizer (B) were excellent in both non-bleeding properties and water resistance. In particular, the test pieces of Example 5 was superior in non-bleeding properties to the test pieces of Comparative Examples 8 and 10.

Moreover, the test pieces of Example 6 prepared using benzyl methyl diglycol adipate as the mixed alcohol ester plasticizer (B) had excellent non-bleeding properties and satisfactory water resistance. These results were superior to those of the test pieces prepared in Comparative Example 9. Further, the test pieces of Example 6 had better non-bleeding properties than those of Comparative Example 10.

TABLE 4

| | | | Ex. 7 | Comp. Ex. 7 | Comp. Ex. 11 | Comp. Ex. 12 |
|---|---|---|---|---|---|---|
| Composition (parts) | (A) Resin component | Polyester | 100 | 100 | 100 | 100 |
| | (B) Plasticizer component | Mixed alcohol 4 | 30 | — | — | — |
| | | Single alcohol 4 | — | — | 30 | — |
| | | Single alcohol 5 | — | — | — | 15 |
| Properties | Non-bleeding properties | | A | — | B | C |
| | Water resistance | | A | — | C | A |
| | Tensile modulus | kgf/cm$^2$ | 1359 | 3640 | 1330 | 1879 |
| | Elongation | % | 500 | 200 | 500 | 500 |

(Mixed alcohol: Mixed alcohol ester, Single alcohol: Single alcohol ester)

As is apparent from Table 4, the test pieces of Example 7 prepared using ethoxycarbonyl methyl dibutyl citrate (Mixed alcohol ester 4) as the mixed alcohol ester plasticizer (B) were excellent in both non-bleeding properties and water resistance. These results were superior to those of the test pieces of Comparative Examples 11 and 12 prepared using triethoxycarbonyl methyl citrate (Single alcohol ester 4) and tributyl citrate (Single alcohol ester 5), respectively, as plasticizers. Further, the test pieces of Example 7 had a lower tensile modulus than that of Comparative Example 12.

INDUSTRIAL APPLICABILITY

The present invention provides an ester compound that can be freely designed to have characteristics desired in a plasticizer for biodegradable aliphatic polyester resins, a plasticizer for biodegradable aliphatic polyester resins that comprises the ester compound, and a biodegradable resin composition comprising the ester compound as a plasticizer.

More specifically, the present invention provides an ester compound that, when used as a plasticizer for a biodegradable aliphatic polyester resin, makes a biodegradable resin composition that has excellent water resistance and from which the plasticizer is difficult to bleed out; a plasticizer for biodegradable aliphatic polyester resins that comprises the ester compound, and a biodegradable resin composition that has excellent water resistance and from which the plasticizer is difficult to bleed out.

Thus, the biodegradable resin composition prepared using the ester compound of the present invention as a plasticizer can be suitably used as a material for films, sheets, packaging, molded articles, etc.

The invention claimed is:

1. An ester compound selected from the group consisting of methoxycarbonylmethyl dimethyl citrate, methoxycarbonylmethyl diethyl citrate, methoxycarbonylmethyl dibutyl citrate, ethoxycarbonylmethyl dimethyl citrate, ethoxycarbonylmethyl dibutyl citrate, ethoxycarbonylmethyl dioctyl citrate, butoxycarbonylmethyl dimethyl citrate, butoxycarbonylmethyl diethyl citrate, butoxycarbonylmethyl dibutyl citrate, dimethoxycarbonylmethyl monomethyl citrate, dimethoxycarbonylmethyl monoethyl citrate, dimethoxycarbonylmethyl monobutyl citrate, diethoxycarbonylmethyl monomethyl citrate, diethoxycarbonylmethyl monobutyl citrate, diethoxycarbonylmethyl monooctyl citrate, dibutoxycarbonylmethyl monomethyl citrate, dibutoxycarbonylmethyl monoethyl citrate, dibutoxycarbonylmethyl monobutyl citrate, and acetates thereof.

2. A plasticizer for biodegradable aliphatic polyester resins the plasticizer comprising at least one ester compound selected from the group consisting of methoxycarbonylmethyl dimethyl citrate, methoxycarbonylmethyl diethyl citrate, methoxycarbonylmethyl dibutyl citrate, ethoxycarbonylmethyl dimethyl ciitrate, ethoxycarbonylmethyl dibutyl citrate, ethoxycarbonylmethyl dioctyl citrate, butoxycarbonylmethyl dimethvl citrate, butoxycarbonylmethyl diethyl citrate, butoxycarbonylmethyl dibutyl citrate, dimethoxycarbonylmethyl monomethyl citrate, dimethoxycarbonylmethyl monoethyl citrate, dimethoxycarbonylmethyl monobutyl citrate, diethoxycarbonylmethyl monomethyl citrate, diethoxycarbonylmethvl monobutyl citrate, diethoxycarbonylmethyl monooctyl citrate, dibutoxycarbonylmethyl monomethyl citrate, dibutoxycarbonylmethyl monoethyl citrate, dibutoxycarbonylmethyl monobutyl citrate, and acetates thereof.

3. A biodegradable resin composition i) a biodegradable aliphatic polyester resin and (ii) a plasticizer comprising at least one ester compound selected from the group consisting of methyl digycol ethyldiglycol adipate, methyl diglycol butyldiglycol adipate, ethyldiglycol butyldiglycol adipate, benzyl methyl diglycol adipate, benzyl ethyldiglycol adipate, benzyl butyldiglycol adipate, methyl dipropylene glycol ethyl dipropylene glycol adipate, methyl dipropylene glycol butyl dipropylene glycol adipate, ethyl dipropylene glycol butyl dipropylene glycol adipate, benzyl methyl dipropylene glycol adipate, benzyl ethyl dipropylene glycol adipate, and benzyl butyl dipropylene glycol adipate.

4. A biodegradable resin composition comprising (i) a biodegradable aliphatic polyester resin and (ii) a plasticizer comprising at least one ester compound represented by formula (3)

(3)

wherein $R^5$ is H, a $C_{1-5}$ aliphatic acyl group or a $C_{6-12}$ aromatic acyl group $R^6$, $R^7$ and $R^8$ $$-(R^9O)_9R^{10} \quad (4)$$

wherein $R^9$ is a $C_{1-6}$ alkylene group; $R^{10}$ is a $C_{1-0}$ straight- or branched-chain alkyl group, a $C_{6-12}$ aryl group, a $C_{7-15}$ arylalkyl group or a $C_{7-15}$ alkylaryl group; and p is an integer from 0 to 6; and $$-CH_2COO(R^{11}O)_qR^{12} \quad (5)$$

wherein $R^{11}$ is a $C_{1-6}$ alkylene group; $R^{12}$ is a $C_{1-10}$ straight- or branched-chain alkyl group, a $C_{6-12}$ aryl group, a $C_{7-15}$ arylalkyl group or a $C_{7-15}$ alkylaryl group; and q is an integer from 0 to 6;
with the proviso that the compound wherein $R^6$, $R^7$ and $R^8$ are the same is excluded.

5. A biodegradable resin composition according to claim 3, wherein the biodegradable aliphatic polyester resin is at least one member selected from the group consisting of resins obtainable by condensation of hydroxycarboxylic acid(s) and resins obtainable by condensation of aliphatic dicarboxylic acid(s) and aliphatic diol(s).

6. A resin composition according to claim 5, wherein the biodegradable aliphatic polyester resin is a poly(lactic acid).

7. A resin composition according to claim 5, wherein the biodegradable aliphatic polyester resin is polybutylene succinate, polybutylene succinate adipate or a mixture thereof.

8. A method for plasticizing a biodegradable aliphatic polyester resin, the method comprising adding to a biodegradable aliphatic polyester resin at least one ester compound selected from the group consisting of methyl diglycol ethyldiglycol adipate, methyl diglycol butyldiglycol adipate, ethyldiglycol butyldiglycol adipate, benzyl methyl diglycol adipate, benzyl ethyldiglycol adipate, benzyl butyldiglycol adipate, methyl dipropylene glycol ethyl dipropylene glycol adipate, methyl dipropylene glycol butyl dipropylene glycol adipate, ethyl dipropylene glycol butyl dipropylene glycol adipate, benzyl methyl dipropylene glycol adipate, benzyl ethyl dipropylene glycol adipate, and benzyl butyl dipropylene glycol adipate.

9. A method according to claim 8, wherein the biodegradable aliphatic polyester resin is a poly(lactic acid).

10. A method according to claim 8, wherein the biodegradable aliphatic polyester resin is polybutylene succinate, polybutylene succinate adipate or a mixture thereof.

11. A method for plasticizing a biodegradable aliphatic polyester resin, the method comprising adding to a biodegradable aliphatic polyester resin at least one ester compound selected from the group consisting of an ester compound represented by formula (3)

(3)

wherein $R^5$ is H, a $C_{1-5}$ aliphatic acyl group or a $C_{6-12}$ aromatic acyl group; and $R^6$, $R^7$, and $R^8$ each represent a group of formula (4) or (5)

$$-(R^9O)_pR^{10} \quad (4)$$

wherein
$R^9$ is a $C_{1-6}$ alkylene group; $R^{10}$ is a $C_{1-10}$ straight- or branched-chain alkyl group, a $C_{6-12}$ aryl group, a $C_{7-15}$ arylalkyl group or a $C_{7-15}$ alkylaryl group; and p is an integer from 0 to 6; and $$-CH_2COO(R^{11}O)_qR^{12} \quad (5)$$

wherein $R^{11}$ is a $C_{1-6}$ alkylene group; $R^{12}$ is a $C_{1-10}$ straight- or branched-chain alkyl group, a $C_{6-12}$ aryl group, a $C_{7-15}$ arylalkyl group or a $C_{7-15}$ alkylaryl group; and q is an integer from 0 to 6;
with the proviso that the compound wherein $R^6$, $R^7$, and $R^8$ are the same is excluded.

12. A method according to claim 11, wherein the biodegradable aliphatic polyester resin is a poly(lactic acid).

13. A method according to claim 11, wherein the biodegradable aliphatic polyester resin is polybutylene succinate, polybutylene succinate adipate or a mixture thereof.

14. A compound selected from the group consisting of methyl diglycol butyldiglycol adipate, benzyl butyldiglycol adipate, and benzyl methyl diglycol adipate.

15. A biodegradable resin composition according to claim 4, wherein the biodegradable aliphatic polyester resin is at least one member selected from the group consisting of resins obtainable by condensation of hydroxycarboxylic acid(s) and resins obtainable by condensation of aliphatic dicarboxylic acid(s) and aliphatic diol(s).

16. A resin composition according to claim 15, wherein the biodegradable aliphatic polyester resin is a poly(lactic acid).

17. A resin composition according to claim 15, wherein the biodegradable aliphatic polyester resin is polybutylene succinate, polybutylene succinate adipate or a mixture thereof.

* * * * *